(12) United States Patent
Carter

(10) Patent No.: US 7,939,109 B1
(45) Date of Patent: May 10, 2011

(54) METHOD OF TREATING NEOPLASTIC DISEASE IN A HUMAN OR ANIMAL PATIENT

(76) Inventor: John Carter, Middlesex (GB)

( * ) Notice: Subject to any disclaimer, the term of this patent is extended or adjusted under 35 U.S.C. 154(b) by 251 days.

(21) Appl. No.: 10/089,846

(22) PCT Filed: Oct. 2, 2000

(86) PCT No.: PCT/GB00/03770
§ 371 (c)(1),
(2), (4) Date: Jun. 6, 2002

(87) PCT Pub. No.: WO01/24803
PCT Pub. Date: Apr. 12, 2001

(30) Foreign Application Priority Data

Oct. 4, 1999 (GB) .................................... 9923431.2
Jun. 13, 2000 (GB) .................................... 0014420.4

(51) Int. Cl.
| | |
|---|---|
| *A61K 33/34* | (2006.01) |
| *A61K 31/19* | (2006.01) |
| *A61K 31/455* | (2006.01) |
| *A61K 31/513* | (2006.01) |
| *A61K 31/60* | (2006.01) |
| *A61K 33/04* | (2006.01) |
| *A61K 33/26* | (2006.01) |
| *A61K 33/30* | (2006.01) |
| *A61K 33/32* | (2006.01) |
| *A61P 3/02* | (2006.01) |
| *A61P 35/00* | (2006.01) |

(52) U.S. Cl. ........ 424/638; 424/630; 424/639; 424/641; 424/646; 424/703; 514/159; 514/274; 514/356; 514/474; 514/557; 514/561

(58) Field of Classification Search .................. 514/159, 514/161, 162, 163, 164, 256, 269, 274, 474, 514/492, 494, 499, 500, 502, 557, 561; 424/705
See application file for complete search history.

(56) References Cited

U.S. PATENT DOCUMENTS

| | | | | |
|---|---|---|---|---|
| 4,061,741 | A | * 12/1977 | Wawretschek et al. | ........ 514/161 |
| 4,514,421 | A | * 4/1985 | Herschler | ...................... 514/711 |
| 4,616,039 | A | * 10/1986 | Herschler | ...................... 514/711 |
| 4,853,377 | A | 8/1989 | Pollack | .......................... 514/116 |
| 4,985,257 | A | * 1/1991 | Verde | ............................ 424/705 |
| 5,290,571 | A | * 3/1994 | Bounous et al. | .............. 424/535 |
| 5,654,011 | A | * 8/1997 | Jackson et al. | ................ 424/635 |
| 5,770,215 | A | 6/1998 | Moshyedi | ....................... 424/440 |
| 5,948,443 | A | 9/1999 | Riley et al. | ..................... 424/643 |
| 6,451,341 | B1 | * 9/2002 | Slaga et al. | .................... 424/468 |

FOREIGN PATENT DOCUMENTS

| | | | |
|---|---|---|---|
| DE | 2457524 | A * | 6/1976 |
| DE | 198 55 426 | A1 | 6/2000 |
| EP | 511895 | A1 * | 11/1992 |
| EP | 0 842 664 | A1 | 5/1998 |
| EP | 0 987 021 | A1 | 3/2000 |

OTHER PUBLICATIONS

Klampfer et al., Blood (Apr. 1999), vol. 93, No. 7, pp. 2386-2394.*
PUBMED online, file MEDLINE, PMID 9923964 (Menon et al., Cancer Biochem. Biophys. (1998), vol. 16, No. 1-2, pp. 17-30), Abstract.*
Maramag et al., Effect of Vitamin C on Prostate Cancer Cells In Vitro: Effect on Cell Number, Viability, and DNA Synthesis, Prostate(1997), vol. 32, pp. 188-195.*
Diril, N. et al., Toxicol. Environ. Chem., 52(1-4), pp. 215-220 (1995).

* cited by examiner

*Primary Examiner* — Sreeni Padmanabhan
*Assistant Examiner* — Frank I Choi

(57) ABSTRACT

A method of treating neoplastic disease in a human or animal patient is provided comprising administering to the patient an anti-neoplastic effective amount of a composition comprising as the sole pharmaceutically active components (a) copper gluconate or copper orotate; (b) sodium salicylate; (c) vitamin C; (d) manganese gluconate or manganese orotate; and optionally one or more of (e) iron gluconate or iron orotate; (f) sublimed sulphur; and (g) zinc gluconate or zinc orotate.

15 Claims, 3 Drawing Sheets

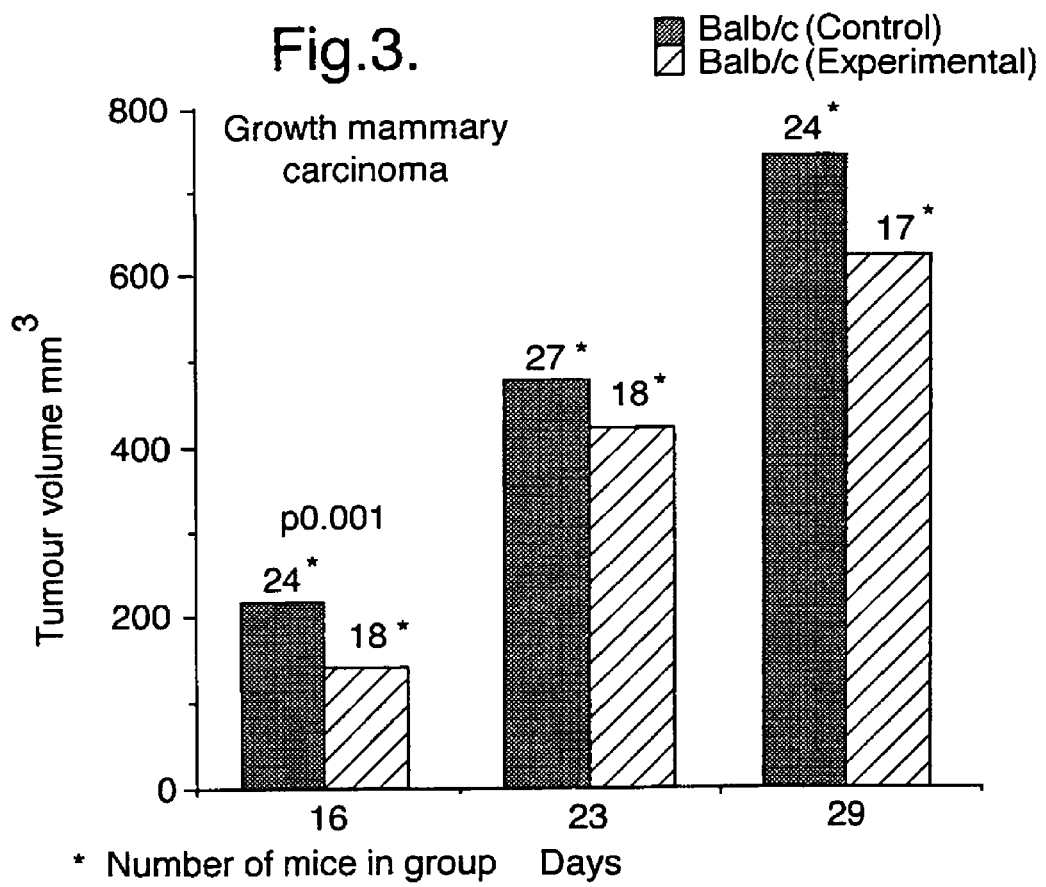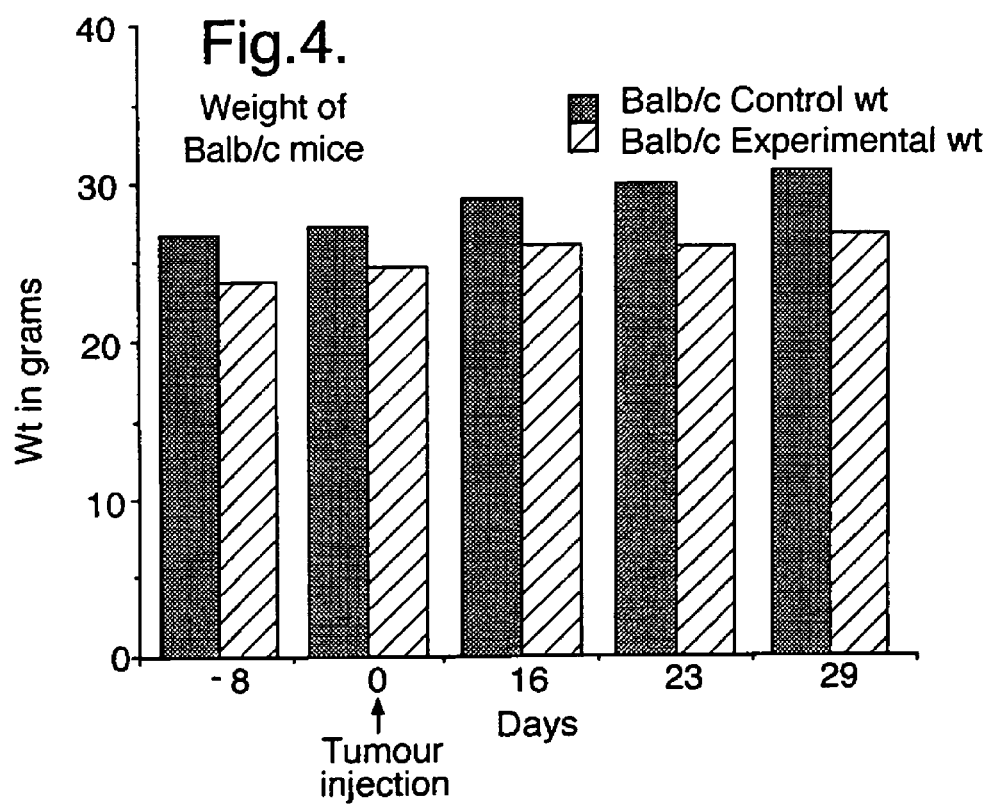

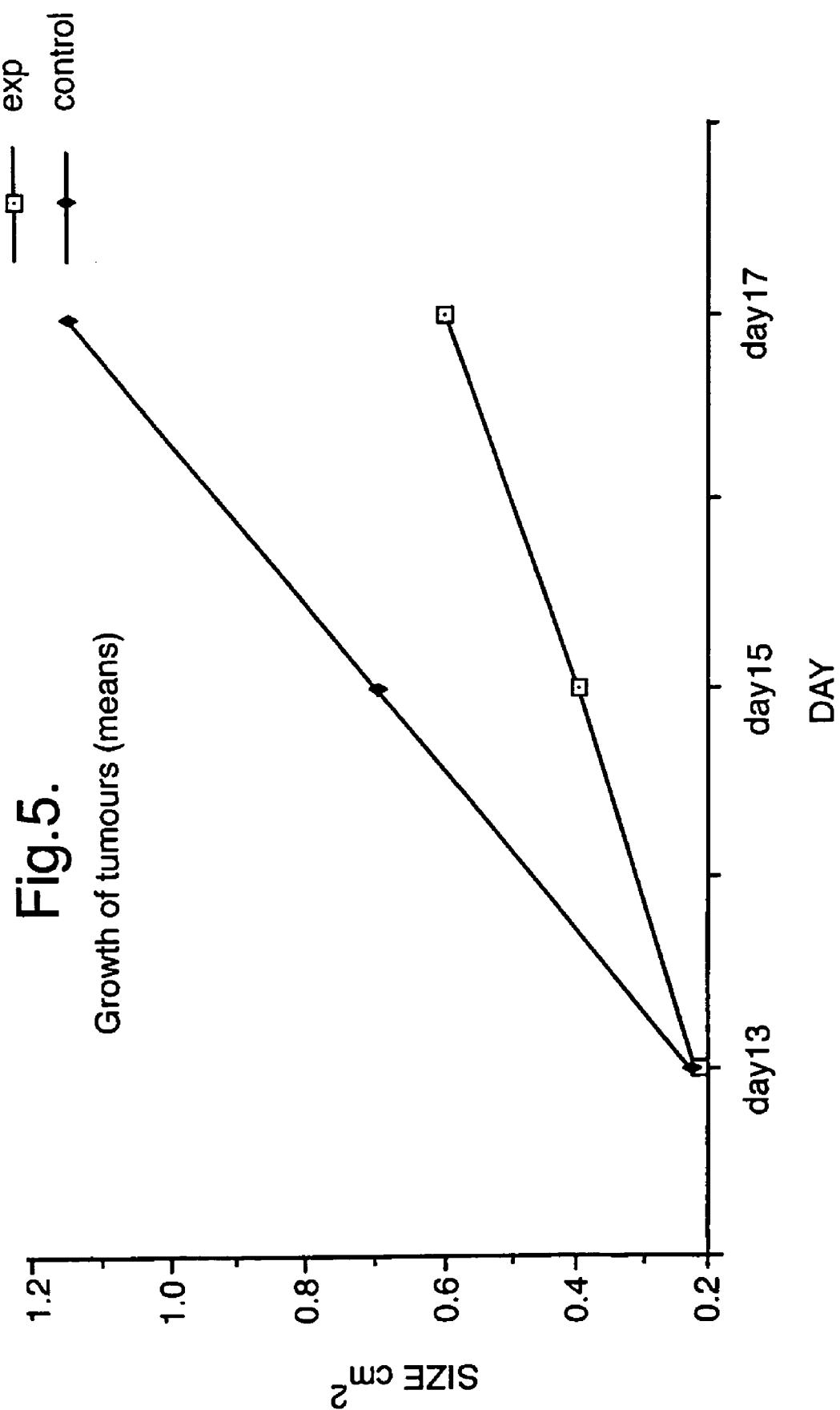

METHOD OF TREATING NEOPLASTIC DISEASE IN A HUMAN OR ANIMAL PATIENT

This application is a national stage application of PCT application PCT/GB00/03770, filed Oct. 2, 2002, claiming priority of UK application No. 9923431.2, filed Oct. 4, 1999, and UK application No. 0014420.4, filed Jun. 13, 2000.

This invention relates to pharmaceutical compositions and their use in the treatment of neoplastic disease.

There has long been a demand for a safe and effective treatment of neoplastic disease. WO 84/04922 proposes the use of copper salicylate complexes for this purpose. However, the copper salicylate complexes of WO 84/04922 are not sufficiently effective to be put to widespread use.

It has now unexpectedly been discovered that a composition comprising an assimilable copper compound, a source of salicylic acid or a derivative thereof and vitamin C, is particularly effective in the treatment of neoplastic disease.

The present invention therefore provides a composition comprising:
(a) a physiologically acceptable source of assimilable copper;
(b) a source of salicylic acid or a physiologically acceptable derivative thereof; and
(c) vitamin C.

Addition of vitamin C to components (a) and (b) leads to a synergistic increase in effectiveness.

Preferably, the composition of the invention further comprises (d), a physiologically acceptable source of assimilable manganese. Alternatively, the composition of the invention may further comprise (e), a physiologically acceptable source of assimilable iron or (f), a physiologically acceptable source of assimilable sulfur. Compositions of the invention comprising both (e) and (f) are particularly preferred.

Particularly preferred compositions of the invention are those comprising:
(a) a physiologically acceptable source of assimilable copper;
(b) a source of salicylic acid or a physiologically acceptable derivative thereof;
(c) vitamin C;
(d) a physiologically acceptable source of assimilable manganese;
(e) a physiologically acceptable source of assimilable iron; and
(f) a physiologically acceptable source of assimilable sulfur.

It has also unexpectedly been found that compositions of the invention further comprising a physiologically acceptable source of assimilable zinc are particularly effective in the treatment of sarcomas.

The present invention therefore also provides a composition of the invention, further comprising a physiologically acceptable source of assimilable zinc.

BRIEF DESCRIPTION OF THE DRAWINGS

FIG. 3 is a bar chart indicating mammary carcinoma growth in the experimental and control mice of Example 12;

FIG. 4 is a bar chart indicating the weight of experimental and control mice of Example 12; and FIG. 5 is a graph indicating the growth of tumors (means) in experimental and control mice of Example 13.

Figure 1:
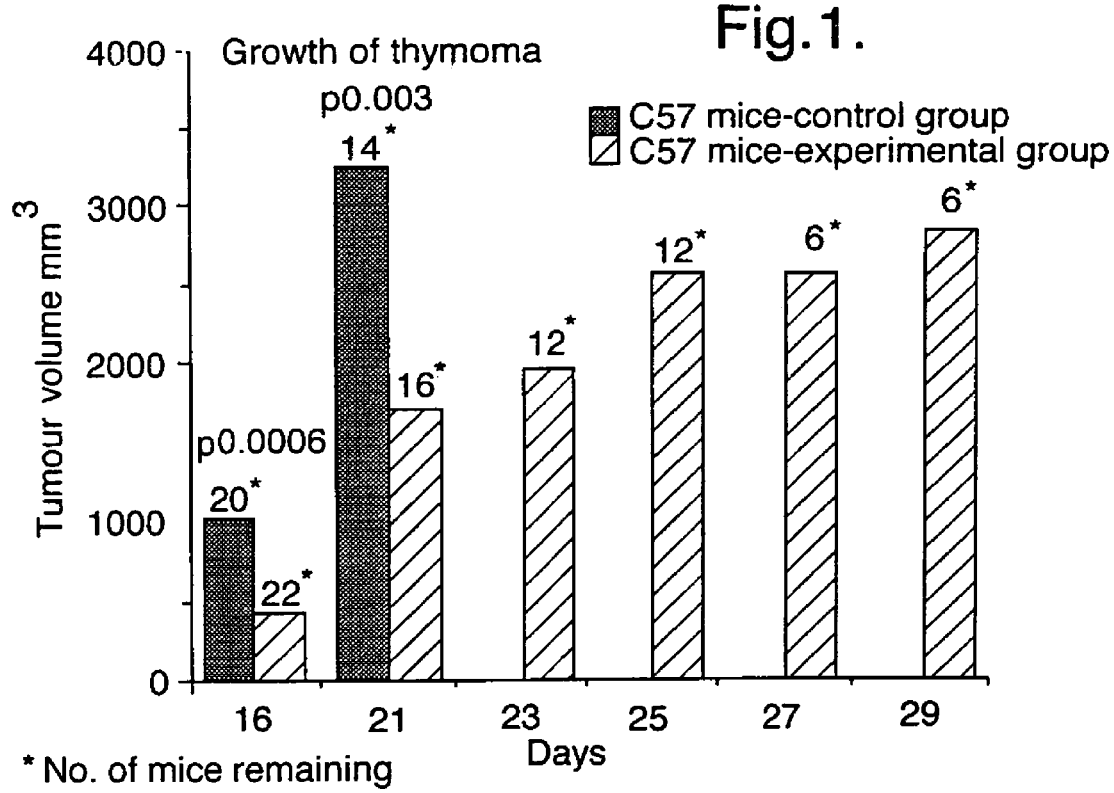
FIG. 1 is a bar chart indicating tumor growth in experimental and control mice in Example 11.

The sources of copper, manganese, iron and zinc used in the composition of the present invention preferably contain the metals in ionic form, e.g. as salts with organic or inorganic acids. However, other metal compounds which provide assimilable sources of the metals, e.g. metal oxides, can also be used.

Thus, a physiologically acceptable source of assimilable copper is typically a copper oxide or a salt of copper with an organic or inorganic acid. A physiologically acceptable source of assimilable manganese is typically a manganese oxide or a salt of manganese with an organic or inorganic acid. A physiologically acceptable source of assimilable iron is typically an iron oxide or a salt of iron with an organic or inorganic acid. A physiologically acceptable source of assimilable zinc is typically a zinc oxide or a salt of zinc with an organic or inorganic acid.

Suitable physiologically acceptable salts of the above metals with organic acids include salts with orotic acid, aspartic acid, gluconic acid, tartaric acid, citric acid, lactic acid, acetic acid, fumaric acid, maleic acid, malic acid, ascorbic acid, succinic acid, benzoic acid, methanesulphonic acid, ethanesulphonic acid, benzenesulphonic acid and p-toluenesulphonic acid. Suitable physiologically acceptable salts of the above metals with inorganic acids include salts with hydrochloric acid, hydrobromic acid, hydriodic acid, phosphoric acid, diphosphoric acid, nitric acid or sulfuric acid, preferably hydrochloric, hydrobromic, hydroiodic, phosphoric or sulfuric acid. Such salts are available commercially or may be prepared if desired by known methods.

Preferred physiologically acceptable salts are salts with organic acids, more preferably salts with orotic acid, aspartic acid, gluconic acid, tartaric acid, citric acid, lactic acid or acetic acid and most preferred are salts with orotic or gluconic acid.

It is also preferred that the physiologically acceptable salts are water soluble, for example salts with gluconic acid.

It is particularly preferred that the physiologically acceptable salt of assimilable copper is copper orotate or copper gluconate, most preferably copper gluconate. It is particularly preferred that the physiologically acceptable salt of assimilable manganese is manganese orotate or manganese gluconate, most preferably manganese gluconate. It is particularly preferred that the physiologically acceptable salt of assimible iron is iron orotate or iron gluconate, most preferably iron gluconate. It is particularly preferred that the physiologically acceptable salt of assimilable zinc is zinc orotate or zinc gluconate, most preferably zinc gluconate.

When, as is preferred, the compositions of the invention contain more than one metal, all the metal salts preferably include the same anion. This anion is typically orotate or gluconate, preferably gluconate.

The source of salicylic acid or a physiologically acceptable derivative thereof is typically salicylic acid or a physiologically acceptable derivative thereof. Typically, the said derivative is a compound in which the carboxyl or hydroxyl function of salicylic acid has been converted into a derivative.

A physiologically acceptable derivative of salicyclic acid is typically a salicylic acid metal salt, ester or amide. Examples of suitable metal salts include alkali metal salts, for example sodium and potassium salts, and alkaline earth metal salts, for example calcium and magnesium salts. Sodium salicylate is most preferable.

Examples of suitable esters include $C_{1-6}$ alkyl esters, for example methyl, ethyl, propyl, butyl, pentyl or hexyl esters and particularly preferred are the methyl and ethyl esters. Examples of suitable amides are amides obtainable by reacting salicylic acid with an amine $HNR_1R_2$, wherein $R_1$ and $R_2$ may be the same or different and are selected from hydrogen and $C_{1-6}$ alkyl groups such as methyl, ethyl, propyl, butyl, pentyl or hexyl. $R_1$ and $R_2$ are preferably selected from hydrogen, methyl and ethyl and most preferably both $R_1$ and $R_2$ are hydrogen.

Derivatives in which both the hydroxyl function and the carboxyl function of salicylic acid have been converted into a derivative can also be used.

When the hydroxyl function of salicyclic acid is converted to a derivative it is typically converted to an ester, for example a $C_1$-$C_6$ alkyl ester such as acetyl-salicylic acid (aspirin).

A particularly preferred derivative of salicylic acid is sodium salicylate.

Salicylic acid itself and suitable derivatives of it are commercially available.

Components (a) and (b) may be present in the composition of the invention as a copper salicylate complex. As used herein, a copper salicylate complex is a complex of copper and salicylic acid or a complex of copper and a said physiologically acceptable derivative of salicylic acid.

Typically, the physiologically acceptable source of assimilable sulfur is elemental sulfur and any allotropic form of sulfur may be used. Preferably, sulfur is present in the composition in the form of sublimed sulfur or precipitated sulfur, most preferably sublimed sulfur.

The compositions of the invention typically comprise 15 to 60, preferably 25 to 40, parts by weight copper gluconate, or equivalent amount of active ingredient when a physiologically acceptable source of assimilable copper other than copper gluconate is used.

Typically, the compositions of the invention comprise from 300 to 600, preferably 300 to 400, most preferably 350, parts by weight sodium salicylate, or equivalent amount of active ingredient when salicylic acid or a physiologically acceptable derivative thereof other than sodium salicylate is used.

Typically, the compositions of the invention comprise from 200 to 1000, preferably 300 to 500, most preferably 400, parts by weight vitamin C. Preferably, vitamin C is present in the compositions of the invention in an amount significantly larger than that which is regarded as the normal minimum daily requirement for an adult.

Typically, the compositions of the invention containing a physiologically acceptable source of assimilable manganese, comprise from 15 to 60, preferably 25 to 40, parts by weight manganese gluconate, or equivalent amount of active ingredient when a physiologically acceptable source of assimilable manganese other than manganese gluconate is used.

Typically, the compositions of the invention containing a physiologically acceptable source of assimilable iron, comprise from 15 to 60, preferably 25 to 40, parts by weight iron gluconate, or equivalent amount of active ingredient when a physiologically acceptable source of assimilable iron other than iron gluconate is used.

Typically, the compositions of the invention containing a physiologically acceptable source of assimilable sulfur, comprise from 15 to 60, preferably 25 to 40, parts by weight sulfur.

Typically, the compositions of the invention containing a physiologically acceptable source of assimilable zinc, comprise from 15 to 60, preferably 25 to 40, parts by weight zinc gluconate, or equivalent amount of active ingredient when a physiologically acceptable source of assimilable zinc other than zinc gluconate is used.

The parts by weight referred to are based on the total weight of these ingredients in the composition.

The amounts of the active ingredients in the compositions of the invention should be calculated having regard to the intended dosage to be administered. When the composition is to be administered orally, as is usual, a suitable dosage is about 2 ml volume for each 60 lbs of body weight of the subject to be treated. This dosage can be administered up to three times a day. The 2 ml volume dosage typically contains from 8 to 35 mg, preferably from 14 to 25 mg of copper gluconate, or an equivalent amount of active ingredient when a physiologically acceptable source of copper other than copper gluconate is used. The 2 ml volume dosage typically contains from 170 to 350 mg, preferably from 170 to 230 mg and most preferably about 200 mg sodium salicylate or an equivalent amount of active ingredient when salicylic acid or a physiologically acceptable derivative thereof other than sodium salicylate is used. The 2 ml volume dosage typically contains from 110 to 570 mg, preferably from 170 to 285 mg and most preferably about 230 mg vitamin C.

A suitable dosage of about 2 ml volume of the compositions of the invention comprising a physiologically acceptable source of assimilable manganese, typically contains from 8 to 35 mg, preferably from 14 to 25 mg of manganese gluconate or an equivalent amount of active ingredient when a physiologically acceptable source of manganese other than manganese gluconate is used.

A suitable dosage of about 2 ml volume of the compositions of the invention comprising a physiologically acceptable source of assimilable iron typically contains from 8 to 35 mg, preferably from 14 to 25 mg of iron gluconate or an equivalent amount of active ingredient when a physiologically acceptable source of iron other than iron gluconate is used.

A suitable dosage of about 2 ml volume of the compositions of the invention comprising a physiologically acceptable source of assimilable sulfur typically contains from 8 to 35 mg, preferably from 14 to 25 mg of sulfur.

A suitable dosage of about 2 ml volume of the compositions of the invention comprising a physiologically acceptable source of assimilable zinc typically contains from 8 to 35 mg, preferably from 14 to 25 mg of zinc gluconate or an equivalent amount of active ingredient when a source of zinc other than zinc gluconate is used.

These figures are approximate and considerable variation in the proportions of the active ingredients is possible without losing the valuable properties of the compositions.

The compositions of the invention may be made by first forming an intimate mixture of the metals to be used in the form of suitable salts or other derivatives, together with sulfur, if present. This mixture in finely ground form can then be added to an aqueous solution or suspension of the salicylic acid or derivative thereof. Typically, from 2 to 5 ml, preferably about 3½ ml of aqueous solution or suspension is used. This solution preferably contains 5-20%, preferably about 10%, by weight of salicylic acid or derivative. The vitamin C may be added before or after the salicylic acid solution, and is preferably added before the salicylic acid solution such that all of the solid ingredients are combined first. The resulting slurry or solution may be administered orally.

The compositions of the invention are thought to work by promoting the formation of the enzyme superoxide dismutase (SOD). SOD functions as a free radical scavenger and reduces DNA damage caused by free radical attack.

The compositions of the invention may be used in human and veterinary medicine, for example in the treatment of cats and dogs. They are useful in the treatment or prevention of a neoplastic disease. They are capable of improving the condition of a patient suffering from a cancer.

Typically, a human or animal is treated by initially administering said dosage of 2 ml of the composition of the invention, comprising active ingredients in the amounts set out above, in the form of an aqueous solution or suspension, per 60 lbs body weight of subject followed by a half dose of a similar solution or suspension 1 to 2 hours later. Four hours later a further half dose may be given. Subsequent treatment (when the tumour has noticeably regressed and/or the symptoms have been considerably alleviated) may consist of the oral administration of 2 ml of the said solution or suspension per 60 lbs body weight of subject once a day. This may be given for three weeks, then, if further progress has been made, the dose may be reduced to 2 ml per 60 lbs body weight on alternate days for 3 weeks. The frequency of dosing may be further reduced as further progress is made.

The compositions of the invention have been found effective in treatment of carcinomas of the breast, rectum, bladder, liver, peritoneum, stomach and urethra, and in some lymphomas. Compositions of the invention comprising a physiologically acceptable source of assimilable zinc are effective against sarcomas. The treatment may be continued until there is a marked regression in the size of the tumour or until the tumour disappears.

The compositions of the invention are normally administered orally. Preferably, therefore they are suitable for oral administration. Suitable forms for oral administration include, for example, tablets, troches, lozenges, aqueous or oily suspensions, dispersible powders or granules. Preferred forms for oral administration are tablets and capsules. However, other routes of administration may be possible provided suitable precautions are taken to make the compositions suitable for administration in the contemplated way. For example, the compositions of the invention may be administered parenterally, whether subcutaneously, intravenously, intramuscularly, intrasternally, transdermally or by infusion techniques, or as a suppository.

It has been found that the effectiveness of the compositions of the invention can be enhanced if they are administered in conjunction with a dietary regime which is low in salt and high in potassium and essential amino acids such as proline, serine, glutamine, lysine, histidine, alanine, methionine and leucine. By way of example, vegetables and fruit may be mentioned as foods which have high potassium content. Porridge oats, for example, have a high potassium, low salt content. By way of example, liver may be mentioned as a food source rich in essential amino acids. Typically, for a human patient about 2 oz of liver per day has been found to be sufficient.

It has been found also that better results are obtained by supplementing the diet of a subject with additional vitamin C, i.e. vitamin C in addition to that preferably contained in the compositions of the invention. For example, the administration of 1 g of vitamin C per 20 lbs subject body weight per day, has been found to enhance the activity of the new compositions. Likewise, administration of nicotinic acid, for example 25 mg per 14 lbs subject body weight per day, has been found to give rise to improved activity of the compositions of the invention.

The following Examples illustrate the invention.

EXAMPLE 1

Copper (II) orotate (35 mg) and manganese (II) orotate (35 mg), in finely divided form were mixed dry. Sodium salicylate solution (3.5 ml of a 10% aqueous solution) was then added followed by vitamin C (400 mg). The resulting suspension is suitable for immediate oral administration.

EXAMPLE 2

Copper (II) orotate (35 mg), manganese (II) orotate (35 mg) and zinc orotate (35 mg) in finely divided form were mixed dry. 3.5 ml of a 10% aqueous solution of sodium salicylate (i.e. 3.5 ml of an aqueous solution containing 350 mg sodium salicylate) was then added followed by vitamin C (400 mg). The resulting suspension is suitable for immediate oral administration.

EXAMPLE 3

To copper (II) orotate (35 mg) in finely divided form was added sodium salicylate solution (3.5 ml of a 10% aqueous solution) followed by vitamin C (400 mg). The resulting suspension is suitable for immediate oral administration.

EXAMPLE 4

Copper (II) orotate (35 mg), manganese (II) orotate (35 mg), iron (II) orotate (35 mg) and sublimed sulfur (35 mg), in finely divided form were mixed dry. Sodium salicylate solution (3.5 ml of a 10% aqueous solution) was then added followed by vitamin C (400 mg). The resulting suspension is suitable for immediate oral administration.

EXAMPLE 5

Copper (II) orotate (35 mg), manganese (II) orotate (35 mg), iron (H) orotate (35 mg), sublimed sulfur (35 mg) and zinc orotate (35 mg) in finely divided form were mixed dry. 3.5 ml of a 10% aqueous solution of sodium salicylate (i.e. 3.5 ml of an aqueous solution containing 350 mg sodium salicylate) was then added followed by vitamin C (400 mg). The resulting suspension is suitable for immediate oral administration.

EXAMPLE 6

Copper (II) gluconate (35 mg), vitamin C (400 mg) and manganese (II) gluconate (35 mg), in finely divided form were mixed dry. Sodium salicylate solution (3.5 ml of a 10% aqueous solution) was then added. The resulting solution is suitable for immediate oral administration.

EXAMPLE 7

Copper (II) gluconate (35 mg), vitamin C (400 mg), manganese (II) gluconate (35 mg) and zinc gluconate (35 mg) in finely divided form were mixed dry. 3.5 ml of a 10% aqueous solution of sodium salicylate (i.e. 3.5 ml of an aqueous solution containing 350 mg sodium salicylate) was then added. The resulting solution is suitable for immediate oral administration.

EXAMPLE 8

To copper (II) gluconate (35 mg) and vitamin C (400 mg) in finely divided form was added sodium salicylate solution (3.5 ml of a 10% aqueous solution). The resulting solution is suitable for immediate oral administration.

EXAMPLE 9

Copper (II) gluconate (35 mg), vitamin C (400 mg), manganese (II) gluconate (35 mg), iron (II) gluconate (35 mg) and sublimed sulfur (35 mg), in finely divided form were mixed dry. Sodium salicylate solution (3.5 ml of a 10% aqueous solution) was then added. The resulting suspension is suitable for immediate oral administration.

EXAMPLE 10

Copper (II) gluconate (35 mg), vitamin C (400 mg), manganese (II) gluconate (35 mg), iron (II) gluconate (35 mg), sublimed sulfur (35 mg) and zinc gluconate (35 mg) in finely divided form were mixed dry. 3.5 ml of a 10% aqueous solution of sodium salicylate (i.e. 3.5 ml of an aqueous solution containing 350 mg sodium salicylate) was then added. The resulting suspension is suitable for immediate oral administration.

EXAMPLE 11

This experiment was conducted at University College London under Home Office License. In this experiment 100 C57B1 male mice were injected subcutaneously with a transplantable RMA thymoma tumour. 50 of the mice were used as controls and 50 mice were experimental mice.

Mice have a much faster rate of metabolism than larger mammals. It was therefore decided to give the mice a larger dose of the formula than the dose which would be suitable for larger animals such as cats and dogs. This latter dose was accordingly increased by a factor of 10.

For a 30 g mouse, 0.022 ml of the solution prepared in Example 1 was administered. This was administered to the mice three times a day at 10 am, 3 pm and 6 pm. The composition was administered by gavage. In addition the experimental mice were fed on a diet of organic wheat, barley, oats and rye.

The general condition of the experimental and control mice following tumour injection is shown in Table 1.

TABLE 1

RMA thymoma in C57B1 male mice

| Days after Tumour injection | Control | Experimental |
|---|---|---|
| 16 | All mice have tumours. 2 killed because of large tumour size. | 20/22 with palpable tumours. 2 probably have deep tumours. 1 sick mouse killed. |
| 18 | | 3 mice died as a result of treatment. 2 with small tumours. 1 had only a large lymph node. |
| 20 | 4 mice killed with large tumours. | 2 sick mice killed, both had tumours. |
| 21 | Remaining mice killed because of large tumours. All tumours firm and infiltrating muscle of thigh or peritoneal wall. | 4 killed with large infiltrating tumours. |
| 23 | | 3/12 mice had superficial freely mobile plaque like tumours. |
| 25 | | 6 mice killed because of large tumour size. All tumours firm and infiltrating. 1 mouse had an axillary abscess. |
| 29 | | 4/6 remaining tumours fixed. Large lymph nodes palpable. |
| 31 | | Remaining mice killed. 5/6 tumours infiltrating deeply. 1/6 more superficial but draining node grossly enlarged. |

Figure 2:
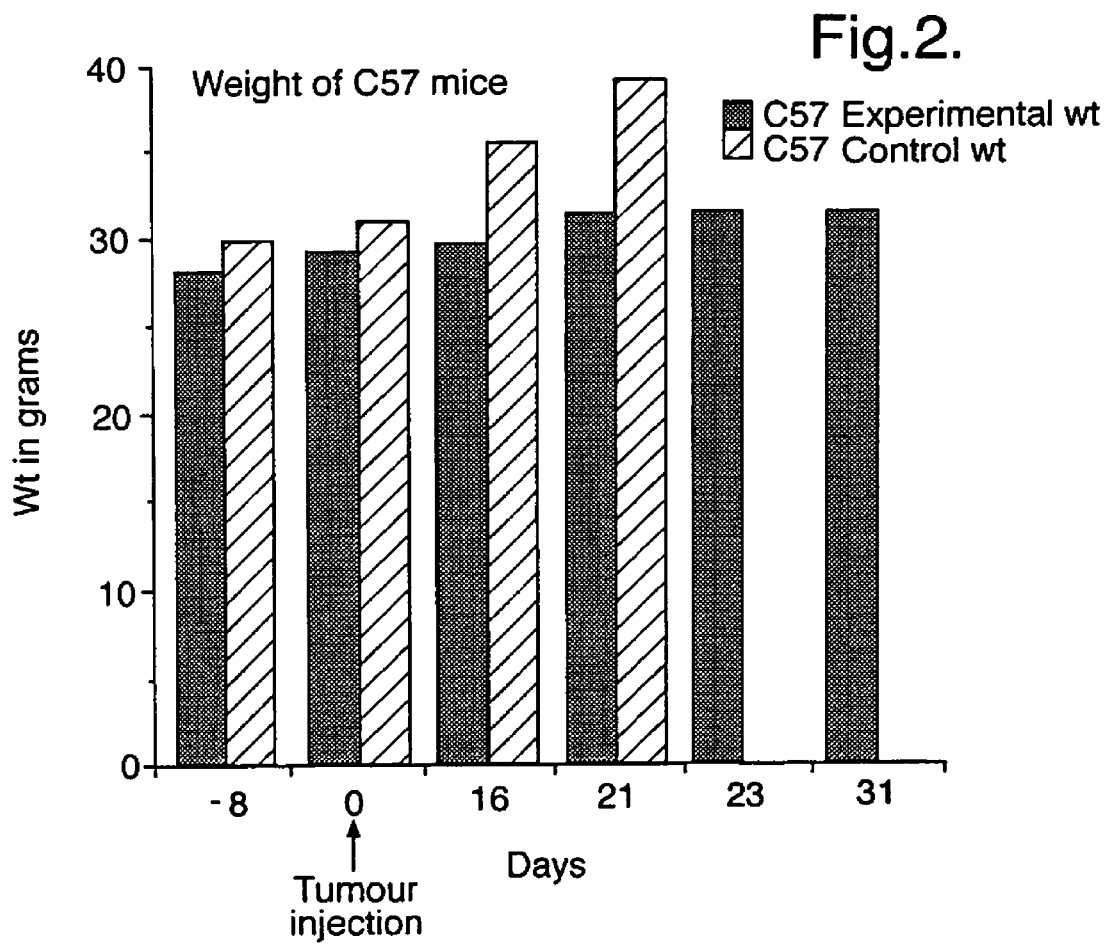
FIG. 2 is a bar chart indicating the weights of the experimental and control mice of Example 11.

The growth of the tumour in experimental and control mice is shown in FIG. 1. The weights of the experimental and control mice are shown in FIG. 2.

The growth of the thymoma tumour was measured by callipers, i.e. the diameter of the surface of the tumour was determined. The tumours were not weighed at the end of the experiment.

As can be seen from FIG. 1, 21 days after tumour injection the tumours in the control mice were approximately 1.9 times larger than those in the experimental mice.

Apart from deaths caused by the stress of gavage, to which the control mice were not subjected, the only side effect observed was slight weight loss, probably attributable to the change of diet.

EXAMPLE 12

This experiment was conducted at University College London under Home Office License. Transplantable mammary carcinomas were injected into 100 male Balb/c mice. 50 of the mice were used as controls and 50 mice were experimental mice.

These tumours grew much more slowly than the thymomas injected in Example 11. Accordingly, less treatment was given to the experimental mice; they were gavaged only once a day with 0.22 ml of the solution prepared in Example 1 and fed on a diet of organic grains as described in Example 11. Nevertheless a result was obtained as can be seen from FIG. 3 showing the growth of the mammary carcinoma in experimental and control mice. But because they were given less treatment the difference in growth rate between the experimental and control groups is much less than that observed in Example 11.

The tumours in the control group were only 1.14 times larger than in the experimental group at 23 days after tumour injection. However, 29 days after tumour injection the tumours in the control group were 1.19 times larger than the tumours in the experimental group.

Apart from deaths caused by the stress of gavage, to which the control mice were not subjected, the only side effect observed was slight weight loss, probably attributable to the change of diet.

EXAMPLE 13

Professor Peter Beverley of the Department of Oncology at University College London Medical School stated that although there was a statistically higher significant effect in tumour growth between the experimental and control mice in Examples 11 and 12, it was clear that the treatment by repeated gavage was stressful so that untreated mice were not a perfect control.

It was therefore decided that a further experiment should be performed but that this time the formula should be administered in the drinking water and given to the mice by gavage only once a day. As a water soluble copper salt was required for addition to the drinking water, it was decided to use copper gluconate in place of copper orotate. The control mice would also have the same organic grains diet as the experimental mice and be gavaged with water once a day. It was also decided that the experimental mice should be given extra vitamin C by having the vitamin C added to their drinking water.

This experiment was conducted at University College London under Home Office License.

Copper (II) gluconate, 35 mg, and manganese (II) orotate, 35 mg, in finely divided form were mixed dry. Sodium salicylate solution (3.5 ml of a 10% aqueous solution) was then added followed by vitamin C (400 mg).

The vitamin C was added to the drinking water of the experimental mice by putting 300 mg of vitamin C in 50 ml of water three times a day. Thus each cc contained 6 mg vitamin C. Each mouse drank on average 4 ml of water containing 24 mg of vitamin C three times a day. So each mouse received on average 72 mg of vitamin C per day.

50 C57B1 male mice were injected subcutaneously with a transplantable thymoma. 24 mice, the experimental mice, were treated, and 26 mice were used as a control.

It was decided to give the mice a larger dose of the formula because they would be gavaged only once a day and it was not sure how much drinking water each mouse would drink.

The dose per mouse compared to larger mammals was now increased by a factor of 17.

Each mouse was gavaged with 0.04 ml of the composition prepared above once a day.

0.5 ml of the composition prepared above was added to the drinking water three times a day. 50 ml of drinking water was provided three times a day. 0.5 ml in 50 ml is 0.01 ml per cc. Each mouse drank approximately 4 ml of water three times a day so each mouse received approximately 0.04 ml of the composition in their drinking water three times a day. Each mouse therefore received approximately a total of 0.04×3=0.12 ml of the composition from the drinking water each day plus 0.04 ml from the gavage, a total of 0.16 ml per day.

During the trial 4 mice from the experimental group and 5 from the control group died because of the gavage. The mice were all killed on day 17 and the tumours were dissected out and weighed. However, two tumours from the control group could not be removed for measurement because they were too extensive. The results are shown in Table 2.

TABLE 2

| Mouse No. | Tumour Weight (g) |
|---|---|
| EXPERIMENTAL GROUP | |
| 1 | .10 |
| 2 | .10 |
| 3 | .20 |
| 4 | .20 |
| 5 | .20 |
| 6 | .30 |
| 7 | .30 |
| 8 | .40 |
| 9 | .40 |
| 10 | .40 |
| 11 | .50 |
| 12 | .50 |
| 13 | .50 |
| 14 | .50 |
| 15 | .50 |
| 16 | .60 |
| 17 | .70 |
| 18 | 1.00 |
| 19 | 1.70 |
| Average tumour weight | 0.48 g |
| CONTROL GROUP | |
| 20 | .40 |
| 21 | .50 |
| 22 | .50 |
| 23 | .60 |
| 24 | .60 |
| 25 | .90 |
| 26 | .90 |
| 27 | .90 |
| 28 | 1.00 |
| 29 | 1.00 |
| 30 | 1.00 |
| 31 | 1.10 |
| 32 | 1.10 |
| 33 | 1.30 |
| 34 | 1.30 |
| 35 | 1.30 |
| 36 | 1.50 |
| 37 | 1.70 |
| 38 | 1.80 |
| 39 | 1.80 |
| Average tumour weight | 1.1 |

It can be seen from Table 2 that the combined weight of tumours from the experimental group was 9.1 grams. The combined weight of the tumours from the control group was 21.2 grams. The control group tumour mass was therefore 21.2/9.1=2.32 times larger than the experimental group tumour mass.

Further, the average tumour weight in the control mice was 1.1 g. The average tumour weight in the experimental mice was 0.48 g.

The average control group tumour mass is therefore 1.1/0.48=2.29 times larger than the average experimental group tumour mass.

The difference in the size of the tumours as measured by callipers during the trial is shown in FIG. 5. It can be seen from FIG. 5 that by day 17 the difference in size between the control and experimental tumours, as measured by callipers, is 8.8/3.6=2.44 times larger. Again there were no detectable side effects.

Professor Beverley has stated that this experiment has confirmed unequivocally that the treatment causes a statistically highly significant difference in tumour growth between the treated and control mice with no detectable side effects.

EXAMPLE 14

A 30 lb 6 year old Manchester Terrier suffering from a spindle cell tumour was treated with the composition described in Example 1.

Before the treatment the animal had a hard lumpy swelling extending over the external side of the left foreleg from below the elbow joint up to the side of the shoulder. This diagnosis was made by Abbey Veterinary Clinics, London, who recommended amputation of the foreleg. 1 cc of the composition was administered orally once a day for 5 days. By the end of 5 days the tumour had reduced in size considerably. The dose was then reduced to 1 cc on alternate days for a further 7 days.

In addition, an extra 3 g vitamin C was administered orally every day and nicotinic acid was administered orally in an amount of 125 mg per day.

A dietary regime was followed of organic fruits, organic vegetables, organic grains and lamb's liver to supply essential amino acids. Salt added to food was avoided.

Following the above treatment, the tumour disappeared. This result was certified by Mr. A. Sebesteny, head vet at the Imperial Cancer Research Fund, Clare Hall Laboratories.

EXAMPLE 15

A 60 lb, 11 year old Doberman bitch was treated with a composition consisting of 30 mg copper orotate, 30 mg manganese orotate, 400 mg vitamin C and 3½ ml of an aqueous solution containing 350 mg sodium salicylate, prepared as in Example 1.

The animal was suffering from a urethral obstruction caused by an infiltrating malignant neoplasm thought to be a transitional cell carcinoma. This diagnosis was made at the department of Clinical Veterinary Medicine, Cambridge University. Before the treatment it could pass only a few drops of water with intense straining.

On the first day of treatment, the animal was given 2 cc of the above composition (administered orally). On the second day it was given 2 cc, followed by 1 cc an hour later, then ½ cc an hour after that. This was repeated every day for a week, after which time an improvement was noted. The dosage was then reduced to 2 cc once a day for a further 3 weeks.

In addition, an extra 6 g vitamin C was administered orally every day and nicotinic acid was administered orally in an amount of 250 mg per day. A dietary regime as set out in Example 14 was followed.

Following the above treatment, the animal showed none of the former symptoms. It was still alive and in excellent health 4 years after the treatment, as can be confirmed by its owner.

EXAMPLE 16

An 80 lb, 6 year old Alsatian was treated with a composition consisting of 50 mg copper orotate, 50 mg manganese orotate, 50 mg zinc orotate, 400 mg vitamin C and 3½ ml of an aqueous solution containing 350 mg sodium salicylate, prepared in the same way as in Example 1, except that the zinc orotate was mixed dry in finely divided form together with the copper and manganese orotate.

The animal was suffering from a nasal tumour, thought to be a sarcoma and could not breathe through its nose. This diagnosis was made by the Department of Small Animal Medicine and Surgery, Royal Veterinary College, London. It had a large, hard, golf-ball sized swelling under the right eye.

It was given 2.6 cc of the above composition, followed by 1.3 cc an hour later (administered orally). This dose was repeated daily for 2 weeks by which time the tumour had significantly regressed, to the extent that the animal could breathe through its nose. The dosage was then reduced to alternate days for a fortnight, then to twice a week, then once a week.

In addition, an extra 8 g vitamin C was administered orally every day and nicotinic acid was administered orally in an amount of 330 mg per day.

A dietary regime as set out in Example 14 was followed.

By the end of the above treatment, the animal was symptom free. This result was certified by Mr. A. Sebesteny, head vet at the Imperial Cancer Research Fund.

EXAMPLE 17

A 60 lb, 7 year old Doberman dog was treated with the composition described in Example 15. It was suffering from carcinoma of the peritoneum. This diagnosis was made by the Department of Small Animal Medicine and Surgery, Royal Veterinary College, London. The animal was in an emaciated state, with a large swelling on the abdomen.

It was treated with 2 cc of the composition, followed by 1 cc an hour later (administered orally) every day for two weeks. After two weeks, the dosage was reduced to 2 cc per day for a further two weeks, followed by a further reduction to 2 cc on alternate days for another two weeks.

In addition, an extra 6 g vitamin C was administered orally each day and nicotinic acid was administered orally in an amount of 250 mg per day.

A dietary regime as set out in Example 14 was followed. After the above treatment the animal was symptom free, as can be confirmed by its owners.

EXAMPLE 18

A 150 lb human male around 45 years old, was treated with the composition described in Example 15. He was suffering from T-cell lymphoma, diagnosed at the Cromwell Hospital, London.

He was given 4.5 cc of the composition (administered orally) once a day for 6 weeks (excluding Sundays). After this time, a regression was noted and the dosage was reduced to alternate days for 2 weeks, followed by a further reduction to once a week for three weeks.

In addition, an extra 15 g of vitamin C was administered orally every day and nicotinic acid was administered orally in an amount of 625 g per day.

A dietary regime as set out in Example 14 was followed. Following the above treatment, all symptoms disappeared. He is still alive and well 6 years after the treatment.

The invention claimed is:

1. A method of treating neoplastic disease in a human or animal patient comprising administering to the patient an anti-neoplastic effective amount of a composition comprising as the sole pharmaceutically active components:
    (a) copper gluconate or copper orotate;
    (b) sodium salicylate;
    (c) vitamin C;
    (d) manganese gluconate or manganese orotate; and optionally one or more of:
    (e) iron gluconate or iron orotate;
    (f) sublimed sulphur; and
    (g) zinc gluconate or zinc orotate.

2. The method of treating neoplastic disease in a human or animal patient according to claim 1 wherein the composition comprises as the sole pharmaceutically active components (a)-(e) and optionally one or both of (f)-(g).

3. The method of treating neoplastic disease in a human or animal patient according to claim 1 wherein the composition comprises as the sole pharmaceutically active components (a)-(d) and (g) and optionally one or both of (e) and (f).

4. The method of treating neoplastic disease in a human or animal patient according to claim 1 wherein:
    the copper gluconate or copper orotate is present in an amount of 15 to 60 parts by weight if copper gluconate, or equivalent amount of active ingredient if copper orotate;
    the sodium salicylate is present in an amount of 300 to 600 parts by weight;
    the vitamin C is present in an amount of 200 to 1000 parts by weight vitamin C, and
    the manganese gluconate or manganese orotate is present in an amount of from 15 to 60 parts by weight if manganese gluconate, or equivalent amount of active ingredient if manganese orotate,
    the parts by weight referred to being based on the total weight of these ingredients in the composition.

5. The method of treating neoplastic disease in a human or animal patient according to claim 4 wherein:
    the copper gluconate or copper orotate is present in an amount of 15 to 40 parts by weight if copper gluconate, or equivalent amount of active ingredient if copper orotate;
    the sodium salicylate is present in an amount of 300 to 400 parts by weight; and
    the vitamin C is present in an amount of 300 to 500 parts by weight.

6. The method of treating neoplastic disease in a human or animal patient according to claim 4 wherein sublimed sulphur is present in an amount of 15 to 60 parts by weight of sulphur.

7. The method of treating neoplastic disease in a human or animal patient according to claim 4 wherein the iron gluconate or iron orotate is present in an amount of 15 to 60 parts by weight if iron gluconate, or equivalent amount of active ingredient if iron orotate, and the sublimed sulphur is present in an amount of 15 to 60 parts by weight of sulphur.

8. The method of treating neoplastic disease in a human or animal patient according to claim 4 wherein the zinc gluconate or zinc orotate is present in an amount of 15 to 60 parts by weight if zinc gluconate, or equivalent amount of active ingredient if zinc orotate.

9. The method of treating neoplastic disease in a human or animal patient according to claim 4 wherein:

the copper gluconate or copper orotate is present in an amount of 15 to 40 parts by weight if copper gluconate, or equivalent amount of active ingredient if copper orotate;

the sodium salicylate is present in an amount of 350 parts by weight;

the vitamin C is present in an amount of 400 parts by weight, and the manganese gluconate or manganese orotate is present in an amount of 15 to 40 parts by weight if manganese gluconate, or equivalent amount of active ingredient if manganese orotate.

10. The method of treating neoplastic disease in a human or animal patient according to claim 9 wherein the sublimed sulphur is present in an amount of 15 to 60 parts by weight of sulphur.

11. The method of treating neoplastic disease in a human or animal patient according to claim 9 wherein the iron gluconate or iron orotate is present in an amount of 15 to 40 parts by weight if iron gluconate, or equivalent amount of active ingredient if iron orotate, and the sublimed sulphur is present in an amount of 15 to 40 parts by weight of sulphur.

12. The method of treating neoplastic disease in a human or animal patient according to claim 9 wherein the zinc gluconate or zinc orotate is present in an amount of 15 to 40 parts by weight if zinc gluconate, or equivalent amount of active ingredient if zinc orotate.

13. The method of treating neoplastic disease in a human or animal patient according to claim 1 wherein the composition is in the form of an orally administrable unit dosage form.

14. The method of treating neoplastic disease in a human or animal patient according to claim 1 wherein the composition comprises as the sole pharmaceutically active components (a)-(d) and (f) and optionally one or both of (e) and (g).

15. The method of treating neoplastic disease in a human or animal patient according to claim 1 wherein the composition comprises as the sole pharmaceutically active components (a)-(d).

* * * * *